US009498191B2

(12) United States Patent
Granger et al.

(10) Patent No.: US 9,498,191 B2
(45) Date of Patent: Nov. 22, 2016

(54) DEVICE AND METHOD FOR USE IN THE COLLECTION OF WHOLE SALIVA IN RESEARCH AND DIAGNOSTICS

(75) Inventors: Douglas A. Granger, Coto de Caza, CA (US); Hans W. Schroeder, Dove Canyon, CA (US)

(73) Assignee: The Johns Hopkins University, Baltimore, MD (US)

( * ) Notice: Subject to any disclaimer, the term of this patent is extended or adjusted under 35 U.S.C. 154(b) by 139 days.

(21) Appl. No.: 14/239,298

(22) PCT Filed: Aug. 16, 2012

(86) PCT No.: PCT/US2012/051052
§ 371 (c)(1),
(2), (4) Date: Apr. 1, 2014

(87) PCT Pub. No.: WO2013/025862
PCT Pub. Date: Feb. 21, 2013

(65) Prior Publication Data
US 2015/0073305 A1    Mar. 12, 2015

Related U.S. Application Data

(60) Provisional application No. 61/524,096, filed on Aug. 16, 2011.

(51) Int. Cl.
*A61B 5/00* (2006.01)
*A61B 10/00* (2006.01)
(52) U.S. Cl.
CPC ........ *A61B 10/0051* (2013.01); *A61B 10/0064* (2013.01)

(58) Field of Classification Search
CPC ............ A61B 10/0045; A61B 10/0051; A61B 10/0064
(Continued)

(56) References Cited

U.S. PATENT DOCUMENTS 3,050,062 A * 8/1962 Ulmer ................. A61M 1/0001
604/76
3,224,434 A * 12/1965 Molomut ............... A61B 10/02
433/91
(Continued)

FOREIGN PATENT DOCUMENTS

WO    9530484 A1    11/1995
WO    0025666 A1    5/2000

*Primary Examiner* — Max Hindenburg
(74) *Attorney, Agent, or Firm* — Johns Hopkins Technology Transfer

(57) ABSTRACT

An embodiment in accordance with the present invention provides a device for collecting a specimen of oral fluids. The device includes an elongate tubular member with a first end being configured to come into contact with a mouth of a subject. The device also includes a coupler, wherein the first end of the coupler is configured to couple to a second end of the elongate tubular member and wherein the second end of the coupler is configured to couple the device to a collection vial. A chamber is defined by the outer wall of the elongate tubular member and positioned proximate to the second end of the elongate tubular member, and a filter is disposed within the chamber. An exhaust port is defined by the coupler to allow pressure to escape from the device to ease the collection of the specimen.

12 Claims, 6 Drawing Sheets

(58) Field of Classification Search
USPC .................................. 600/573, 581; 604/76
See application file for complete search history.

(56) References Cited

U.S. PATENT DOCUMENTS

| | | | | |
|---|---|---|---|---|
| 4,205,690 | A | * | 6/1980 | Layton .................. A61M 39/22 600/581 |
| 4,791,914 | A | * | 12/1988 | May .................... A61M 1/0023 600/573 |
| 4,799,924 | A | * | 1/1989 | Rosenblatt ........... A61M 1/0011 128/201.25 |
| 5,078,603 | A | * | 1/1992 | Cohen .................. A61C 17/043 433/91 |
| 5,268,148 | A | | 12/1993 | Seymour |
| 5,981,293 | A | | 11/1999 | Charlton |
| 6,299,763 | B1 | * | 10/2001 | Ashman ............... A61C 1/0076 210/448 |
| 8,122,890 | B2 | * | 2/2012 | Vaska .................... A61F 5/566 128/200.24 |
| 2004/0022687 | A1 | | 2/2004 | Wuske et al. |

\* cited by examiner

DEVICE AND METHOD FOR USE IN THE COLLECTION OF WHOLE SALIVA IN RESEARCH AND DIAGNOSTICS

CROSS-REFERENCE TO RELATED APPLICATIONS

This application is a 35 U.S.C. §371 U.S. national entry of International Application PCT/US2012/051052 having an international filing date of Aug. 16, 2012, which claims the benefit of U.S. Provisional Application No. 61/524,096, filed Aug. 16, 2011, the content of each of the aforementioned applications is herein incorporated by reference in their entirety.

FIELD OF THE INVENTION

The present invention relates generally to specimen collection. More particularly, the present invention relates to a device and method for collecting saliva samples from a subject.

BACKGROUND OF THE INVENTION

Oral fluid or saliva is a bio-specimen with considerable research and diagnostic potential. At present, the tools and techniques used to collect oral fluids have the potential to introduce error in the measurement of salivary analytes. A common solution to these problems is to have patients and research participants passively drool whole saliva into collection vials. This technique eliminates any possibility of confounding influence on the integrity of the specimen. However, this simple technique is unpalatable to many, can draw unwanted attention to the donor, and can be inappropriate in many everyday settings where saliva collections must take place.

Therefore, an alternative to sampling drooling is to ask that donors gently force saliva into collection containers using short sections of drinking straws. This additional procedure solves a component of the problem but also introduces new issues. To use the "crude straw technique" requires that the donor hold the straw with one hand, and the vial with the other. The straw sections need to be short (typically 2 inches) and that length makes it hard for the donor to coordinate the two units together. More importantly, as air is forced through the straw into the specimen container it creates bubbles and foaming. Bubbles and/or foaming can easily over flow the top of the collection vial, and obscure visibility of the meniscus. The former issue creates a potential biohazard, source of embarrassment, and a need for materials to clean the exterior of the collection device and the surrounding area. The latter makes it difficult for the donor or the health/research professional to determine whether sufficient sample has been received in the vial.

It would therefore be advantageous to provide a device and method to minimize the burden and maximize the palatability of sample donation by creating a self-contained collection system with the vial which minimizes foaming/bubbling during the transfer of oral fluid into the collection vial.

SUMMARY OF THE INVENTION

The foregoing needs are met, to a great extent, by the present invention, wherein in one aspect, a device for collecting a specimen of oral fluids includes an elongate tubular member, having a first end and a second end and an outer wall defining a lumen extending therethrough wherein the first end of the elongate tubular member is configured to come into contact with a mouth of a subject. The device also includes a coupler having a first end and a second end and an outer wall defining a lumen extending therethrough, wherein a first end of the coupler is configured to couple to a second end of the elongate tubular member and wherein the second end of the coupler is configured to couple the device to a collection vial. A chamber is defined by the outer wall of the elongate tubular member and positioned proximate to the second end of the elongate tubular member, and a filter is disposed within the chamber. An exhaust port is defined by the coupler to allow pressure to escape from the device.

In accordance with another aspect of the present invention, the filter further can be formed from a polymer blended foam or other material. The device can also include a treated coupler, wherein the treated coupler can take the form of a coupler treated with at least one selected from the group of a bacteria static agent to enable the specimen to be held at room temperature during transit, dyes to enable the subject to determine how much specimen has been deposited relative to volume requirements, dyes to determine if sample degradation has occurred, and inhibitors to prevent the degradation of analytes of primary interest in the specimen. The exhaust port further can include a channel defined by the outer wall of the coupler. The device can have a volume capacity of approximately 50 µL to 5 mL. The outer wall of the coupler further defines a press fit taper such that the device can be press-fit into collection vials of varying size.

In accordance with another aspect of the present invention, a device for collecting a specimen of oral fluids includes an elongate tubular member, having a first end and a second end and having a lumen extending therethrough wherein the first end of the elongate tubular member is configured to come into contact with a mouth of a subject. A coupler having a first end and a second end and a lumen extending therethrough, is also included. A first end of the coupler is configured to couple to a second end of the elongate tubular member and the second end of the coupler is configured to couple the device to a standard collection vial. A chamber is defined by an outer wall of the elongate tube positioned proximal to the second end of the elongate tube.

In accordance with another aspect of the present invention, a method of depositing an oral fluid sample into a specimen container includes obtaining a device for collection of the oral fluid sample having an elongate tubular member and a coupler for coupling the device to the specimen container. A step includes inserting the device into the specimen container. Another step includes allowing the oral fluid to pool in mouth, and another step includes forcing the oral fluid through the elongate tubular member and into the specimen container. The method also includes filling the specimen container to the predetermined volume.

In accordance with yet another aspect of the present invention, the method can include tearing open a sterile pouch containing the device. Additionally, the method can include attaching a cap to the specimen vial, and disposing of the device.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a device for collecting a specimen of oral fluids. The device includes an elongate tubular member with a first end being configured to come into contact with a mouth of a subject. The device also includes a coupler, wherein the first end of the coupler is configured to couple to a second end of the elongate tubular member and wherein the second end of the coupler is configured to couple the device to a collection vial. A chamber is defined by the outer wall of the elongate tubular member and positioned proximate to the second end of the elongate tubular member, and a filter is disposed within the chamber. An exhaust port is defined by the coupler to allow pressure to escape from the device to ease the collection of the specimen.

Figure 1:
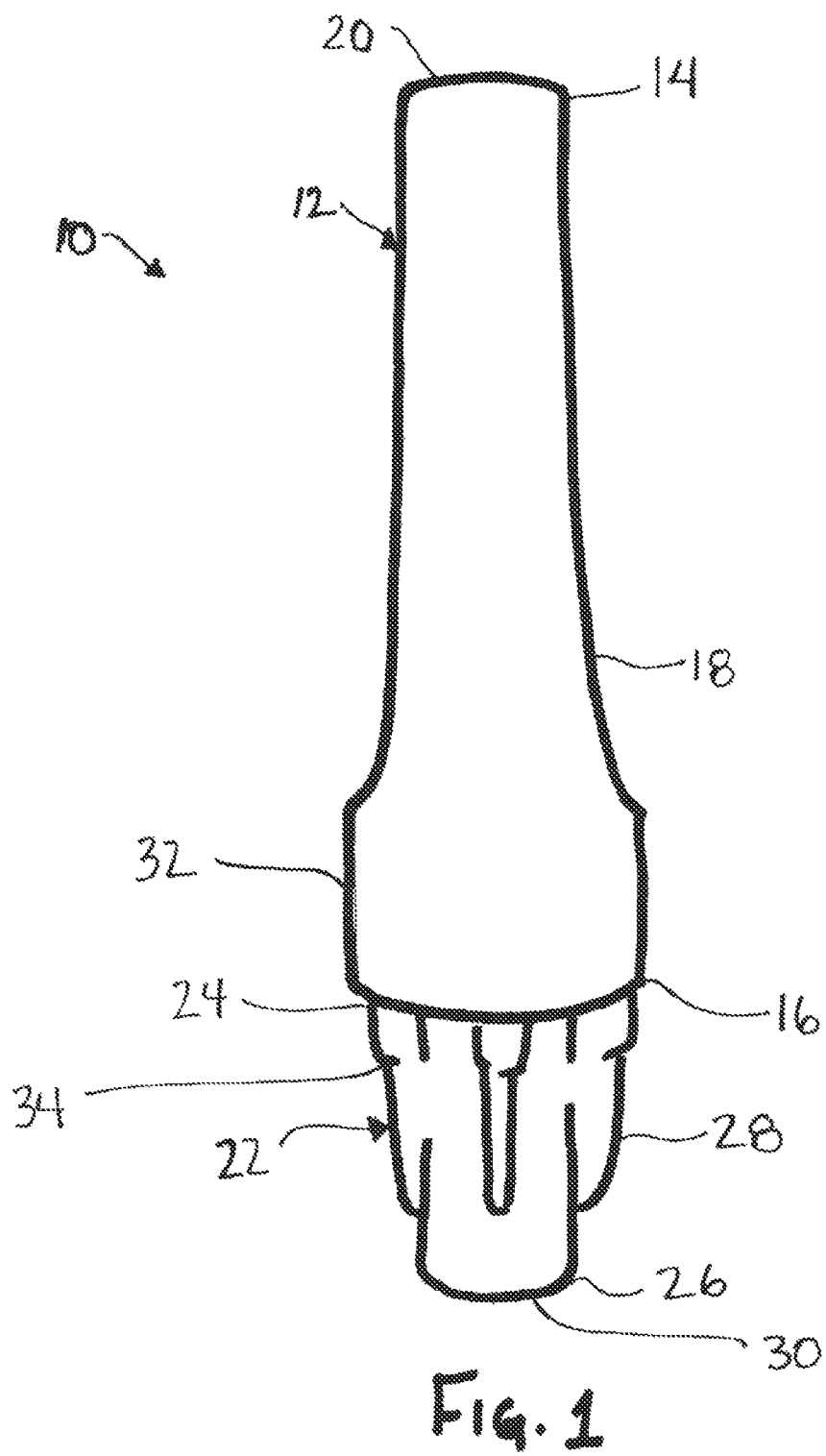
FIG. 1 illustrates a side view of a device for collecting an oral fluid specimen according to an embodiment of the present invention.

FIG. 1 illustrates a side view of a device for collecting an oral fluid specimen according to an embodiment of the present invention. The device 10 includes an elongate tubular member 12 having a first end 14 and a second end 16 and an outer wall 18 defining a lumen 20 extending therethrough. The first end 14 of the elongate tube 12 is configured to come into contact with the mouth of the subject and is further configured to receive oral fluid from the subject and deliver it into the device 10. The device 10 also includes a coupler 22 having a first end 24 and a second end 26. The coupler 22 has an outer wall 28 defining a lumen 30 therethrough. The coupler 22 is coupled to the second end 16 of the elongate tube 20 such that the lumen 20 of the elongate tube 12 is in fluid communication with the lumen 30 of the coupler 22. The second end 26 of the coupler 22 is configured to be coupled to a standard specimen collection vial known to or conceivable by one of skill in the art. The specimen collection vial can hold between approximately 50 µL to 5 mL of specimen. The second end 26 of the coupler can be press fit into the specimen collection vial, or can be coupled to the collection vial in any other means known to or conceivable by one of skill in the art, such as a frictional fit, threads, a luer connector, or any other suitable means. The tube 12 and the coupler 22 can be formed from a clear or opaque plastic material, such as polypropylene, or any other suitable material, known to or conceivable by one of skill in the art.

FIG. 1 also illustrates a chamber 32 defined by the outer wall 18 at the second end 16 of the elongate tubular member 12. The chamber 32 can have a slightly greater diameter than that of the first end 14 of the elongate tube 12. The chamber 32 is further configured to receive a filter (not shown), which will be discussed further herein. The outer wall 28 of the coupler 22 can also define an exhaust port 34 to allow pressure to escape from the device 10. The exhaust port 34 can take the form of a channel or any other suitable configuration known to or conceivable by one of skill in the art. The exhaust port 34 allows the subject to blow the sample through the device 10 and into the specimen container without pressure buildup and potential specimen reflux.

Figure 2:
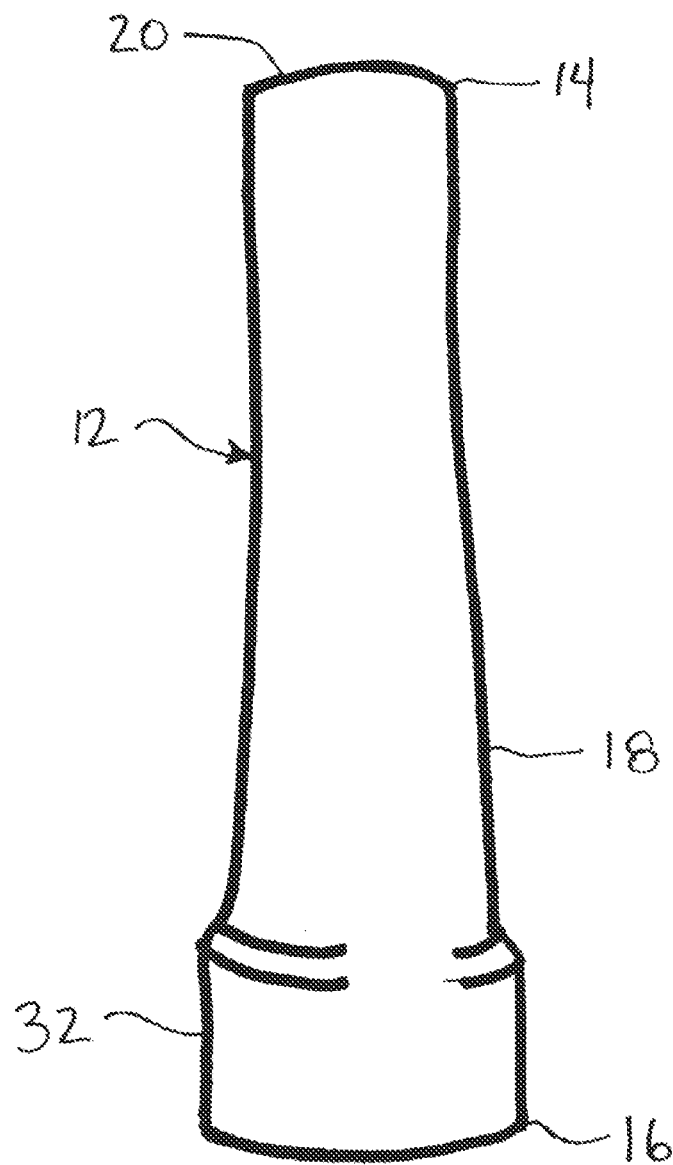
FIG. 2 illustrates a side view of the elongate tube illustrated in FIG. 1, according to an embodiment of the present invention.

FIG. 2 illustrates a side view of the elongate tube 12 illustrated in FIG. 1, according to an embodiment of the present invention. The tube 12 includes the first end 14 and the second end 16 and the outer wall 18 defining a lumen 20 extending therethrough. The first end 14 of the elongate tube 12 is configured to come into contact with the mouth of the subject and is further configured to receive oral fluid from the subject and deliver it into the device 10. The second end 16 is configured to be coupled to the first end of the coupler (not illustrated). As illustrated in FIG. 2 the diameter at the first end 14 of the tube 12 is less than the diameter at the second end 16 of the tube 12. The increased diameter at the second end 16 is such that the tube 12 can accommodate a filter (not illustrated) in the chamber 32 defined by the outer wall 18 of the tube and positioned proximate to the second end 16 of the tube 12.

Figure 3:
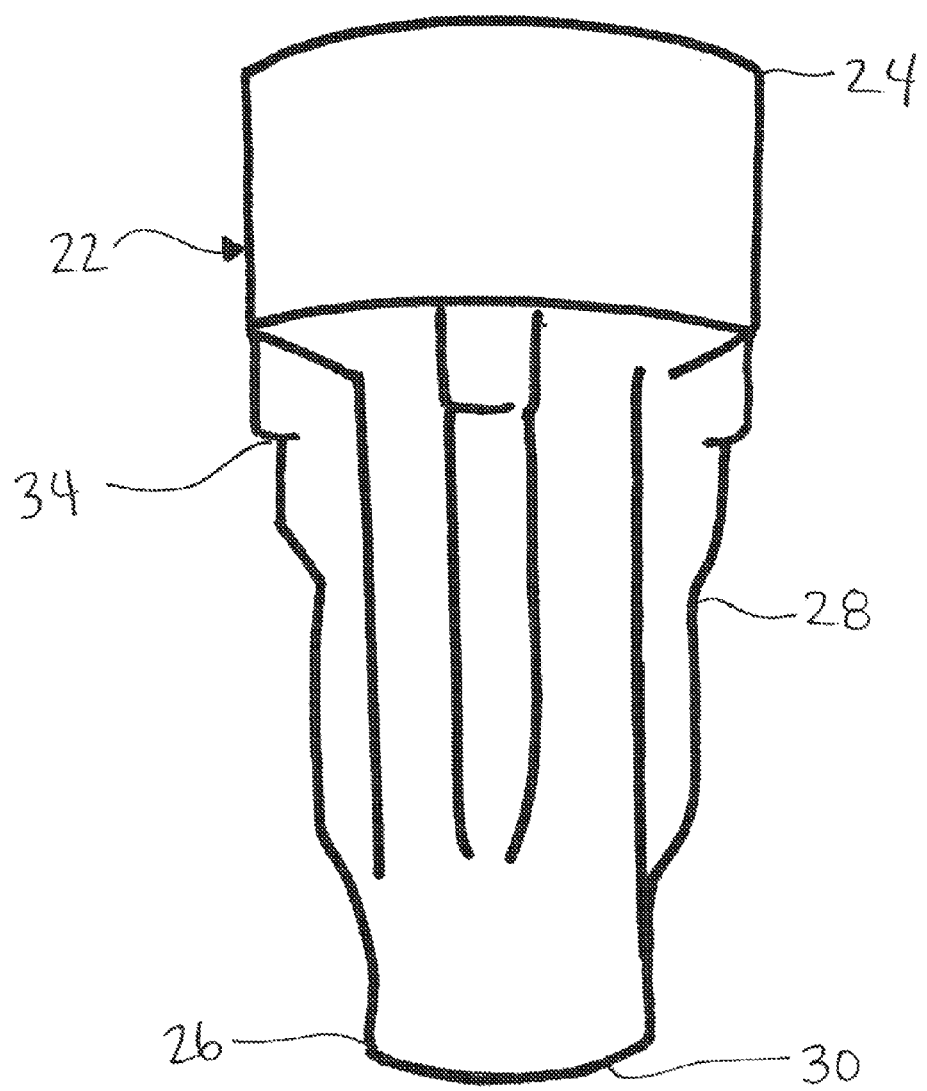
FIG. 3 illustrates a side view of the coupler illustrated in FIG. 1, according to an embodiment of the present invention.

FIG. 3 illustrates a side view of the coupler 22 illustrated in FIG. 1, according to an embodiment of the present invention. The coupler 22 includes the first end 24 and the second end 26. The coupler 22 has the outer wall 28 defining the lumen 30 therethrough. The coupler 22 is coupled to the second end 16 of the elongate tube 12 such that the lumen 20 of the elongate tube 12 is in fluid communication with the lumen 30 of the coupler 22. The second end 26 of the coupler 22 is configured to be coupled to a standard specimen collection vial known to or conceivable by one of skill in the art. The second end 26 of the coupler can be press fit into the specimen collection vial, or can be coupled to the collection vial in any other means known to or conceivable by one of skill in the art, such as a frictional fit, threads, a luer connector, or any other suitable means. The second end 26 of the coupler 22 can also include a taper 34 to facilitate a press fit in specimen vials of varying diameters.

Further, as illustrated in FIG. 3, the outer wall 28 of the coupler 22 can also define the exhaust port 34 to allow pressure to escape from the device 10. The exhaust port 34 can take the form of a channel or any other suitable configuration known to or conceivable by one of skill in the art. The exhaust port 34 allows the subject to blow the sample through the device 10 and into the specimen container without pressure buildup and potential specimen reflux. The coupler 32 can further be treated with different agents to improve sample quality and to maintain sample integrity. These treatments can include, but are not limited to, a bacteria static agent to enable samples to be held at room temperature during transit; dyes to enable the subject to determine quickly how much sample has been donated relative to volume requirements; and inhibitors to prevent the degradation of analytes of primary interest in the specimen. These treatments are merely included by way of example, and should not be considered limiting. Any suitable treatments, known to or conceivable by one of skill in the art, to the coupler 32, the elongate tube 12 or any other component of the device 10 can also be used.

Figure 4:
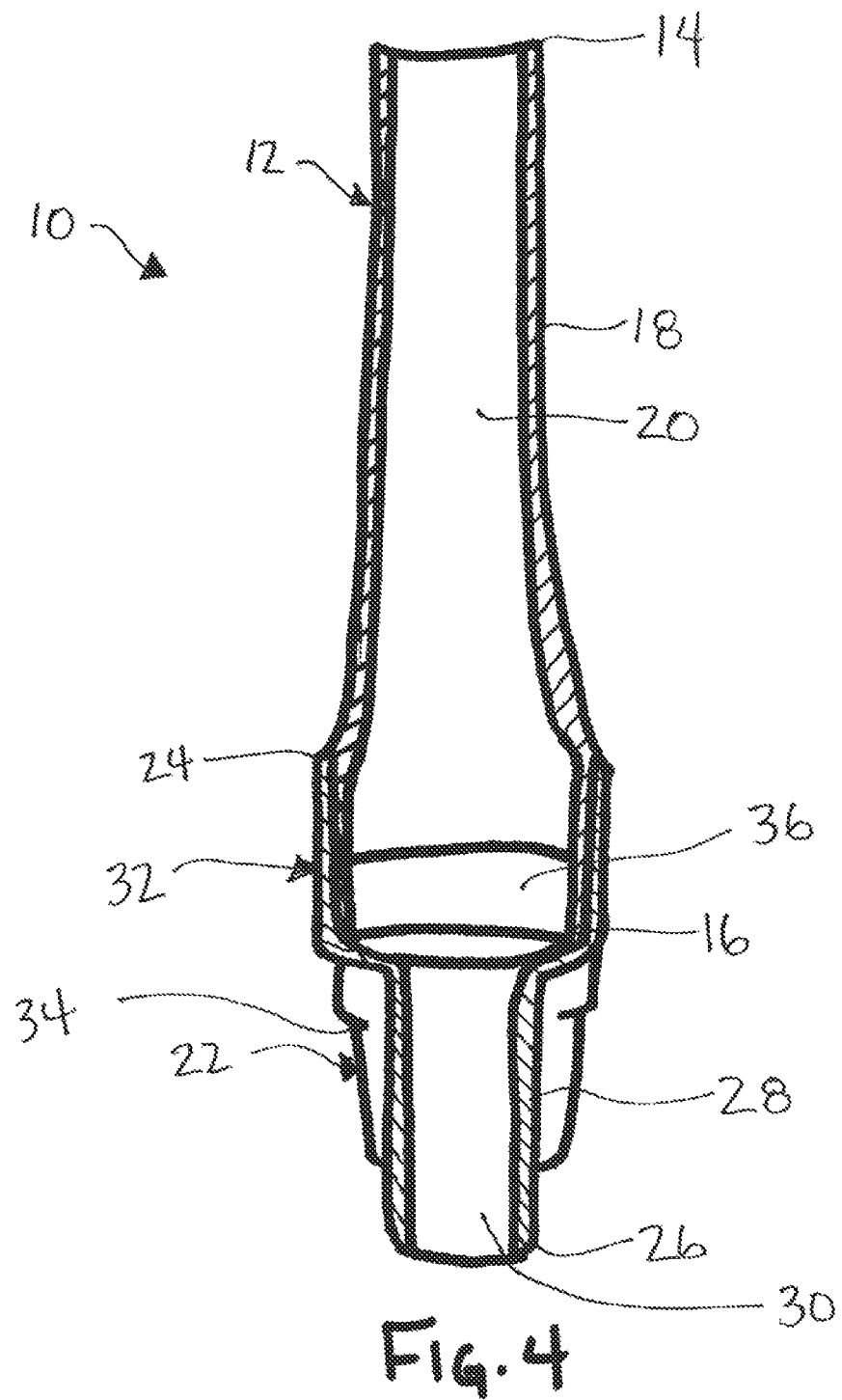
FIG. 4 illustrates a sectional view of the device, according to an embodiment of the present invention.

FIG. 4 illustrates a sectional view of the device 10, according to an embodiment of the present invention. As illustrated in FIG. 4, the second end 16 of the elongate tube 12 nests within the first end 24 of the coupler 22. The outer wall 18 of the second end 16 of the elongate tube 12 and the outer wall 28 of the first end 24 of the coupler 22 also fit together to form the chamber 32. A filter 36 is disposed within the chamber 32. The filter 36 can be approximately 3 mm to 6 mm thick and slightly smaller in diameter than the inside of the chamber 32. The filter 36 can be formed from an inert polymer blended foam or any other suitable material known to or conceivable by one of skill in the art. The filter 36 is configured to remove large macromolecules, such as the carbohydrates that make saliva viscous, from the specimen. The interior of the chamber 32 and the lumens 20 and 30 can also include fluting to minimize bubble formation and to allow for the rapid flow of specimen across its length. The fluting also allows air pressure accumulating in the device 10, to be vented.

Figure 5:
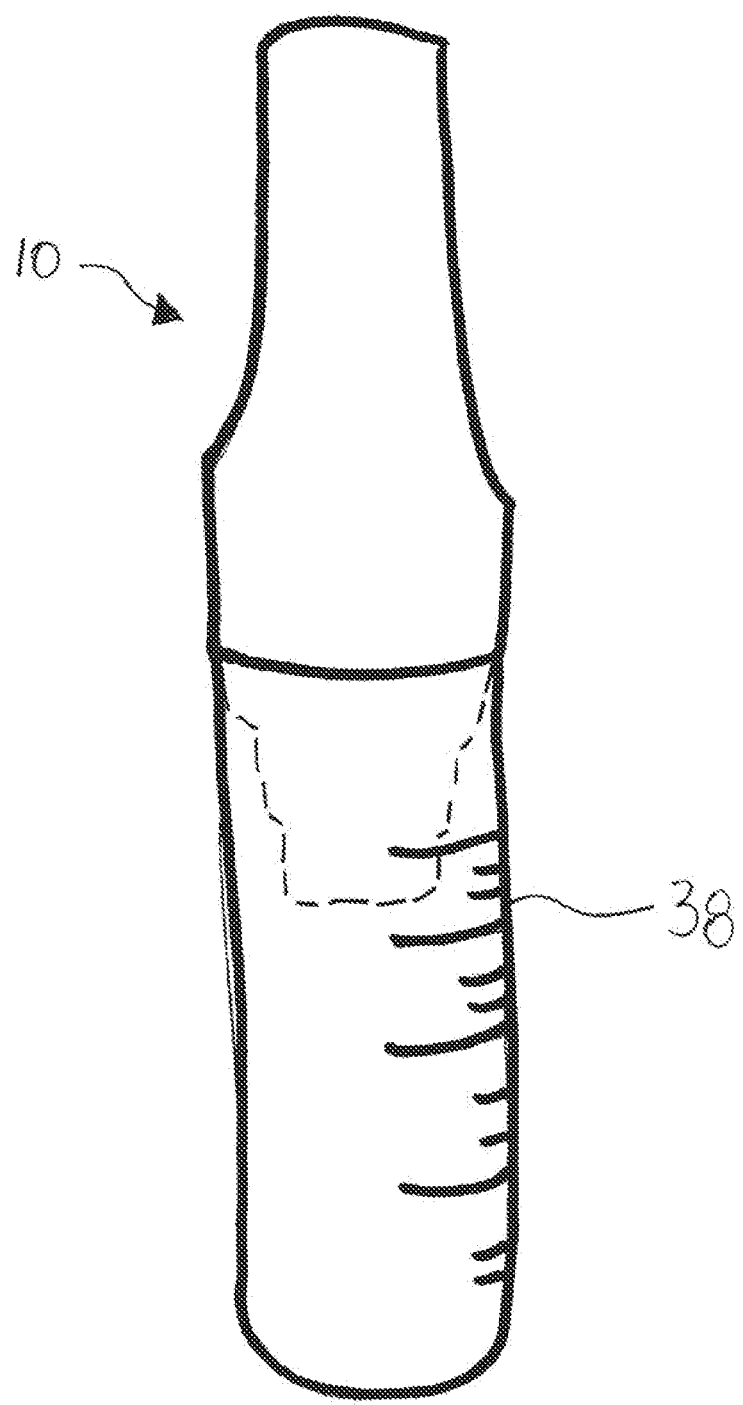
FIG. 5 illustrates a side view of the device for collecting an oral fluid specimen disposed within a specimen collection vial, according to an embodiment of the present invention.

FIG. 5 illustrates a side view of the device for collecting an oral fluid specimen disposed within a specimen collection vial, according to an embodiment of the present invention. As illustrated in FIG. 5 the device 10 is press fit within the specimen vial 38, resulting in an easily removable frictional coupling. As noted above, the specimen vial 38 and the device 10 can also be coupled using different means known to or conceivable by one of skill in the art, such as a different form of frictional fit, a luer connector, threading on the device, etc.

Figure 6:
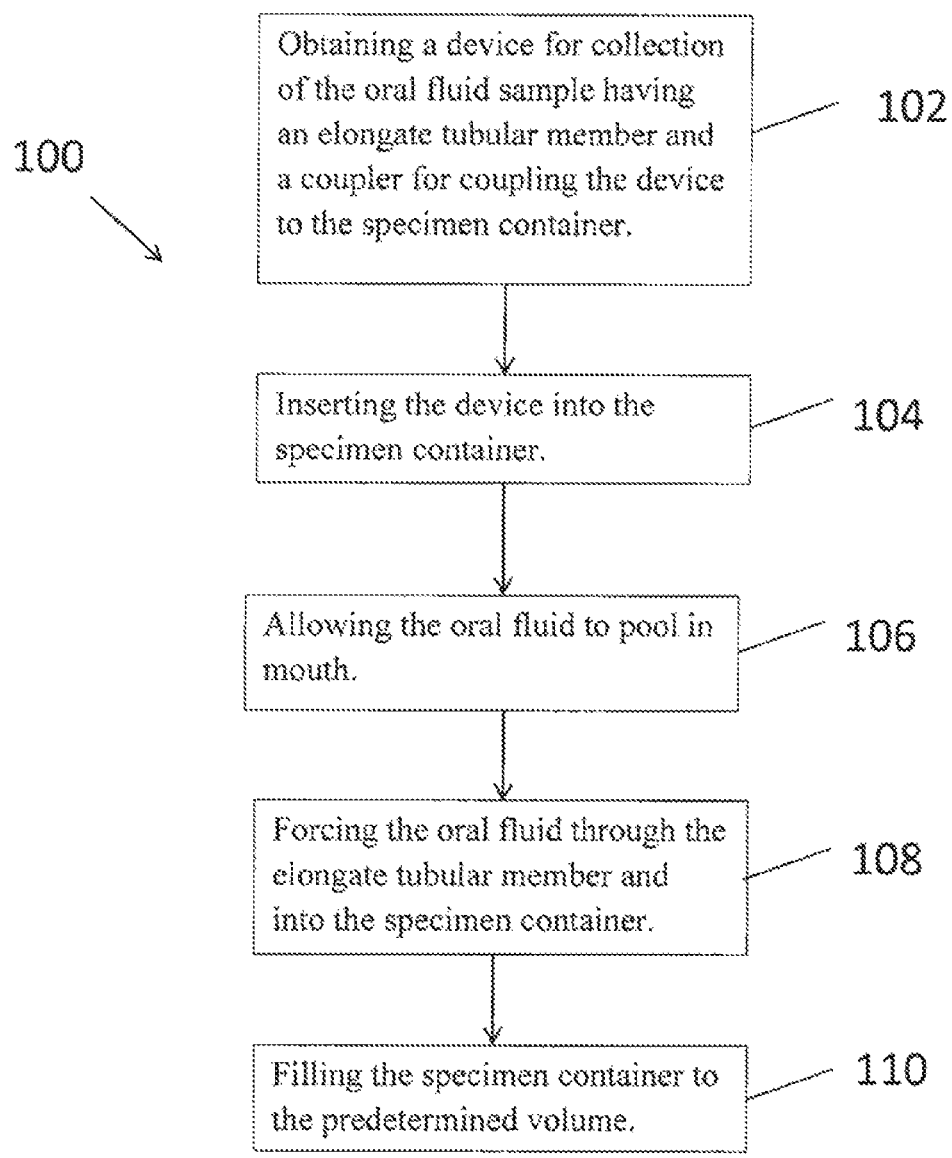
FIG. 6 is a flow diagram illustrating a method of collecting an oral fluid specimen, according to an embodiment of the present invention.

FIG. 6 is a flow diagram illustrating a method of collecting an oral fluid specimen, according to an embodiment of the present invention. As illustrated in FIG. 6 the method of collecting an oral fluid specimen 100 can include step 102 of obtaining a device for collection of the oral fluid sample having an elongate tubular member and a coupler for coupling the device to the specimen container. Step 104 includes inserting the device into the specimen container, and step 106 includes allowing the oral fluid to pool in mouth. A step 108 includes forcing the oral fluid through the elongate tubular member and into the specimen container, and step 110 includes filling the specimen container to the predetermined volume.

The method can further include tearing open a sterile pouch containing the device, and attaching a cap to the specimen vial. The device for collecting an oral fluid specimen can also be disposed of after use of the device.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A device for collecting a specimen of oral fluids comprising:
    an elongate tubular member, having a first end and a second end and an outer wall defining a lumen extending therethrough wherein the first end of the elongate tubular member is configured to come into contact with a mouth of a subject;
    a coupler having a first end and a second end and an outer wall defining a lumen extending therethrough, wherein a first end of the coupler is configured to couple to a second end of the elongate tubular member and wherein the second end of the coupler is configured to couple the device to a collection vial;
    a chamber defined by the outer wall of the elongate tubular member and positioned proximate to the second end of the elongate tubular member;
    a filter disposed within the chamber;
    an exhaust port defined by the coupler to allow pressure to escape from the device; and
    a treated coupler wherein the treated coupler further comprises the coupler treated with at least one selected from the group of a bacteria static agent to enable the specimen to be held at room temperature during transit, dyes to enable the subject to determine how much specimen has been deposited relative to volume requirements, dyes to determine if sample degradation has occurred, and inhibitors to prevent the degradation of analytes of primary interest in the specimen.

2. The device of claim 1 wherein the filter further comprises a polymer blended foam or other material.

3. The device of claim 1 wherein the exhaust port further comprises a channel defined by the outer wall of the coupler.

4. The device of claim 1 further comprising a specimen collection vial having a volume capacity of approximately 50 µL to 5 mL.

5. The device of claim 1 wherein the outer wall of the coupler further defines a press fit taper such that the device can be press-fit into collection vials of varying size.

6. A device for collecting a specimen of oral fluids comprising:
    an elongate tubular member, having a first end and a second end and having a lumen extending therethrough wherein the first end of the elongate tubular member is configured to come into contact with a mouth of a subject;
    a treated coupler having a first end and a second end and a lumen extending therethrough, wherein a first end of the treated coupler is configured to couple to a second end of the elongate tubular member and wherein the second end of the treated coupler is configured to couple the device to a standard collection vial; and
    wherein the treated coupler further comprises the coupler treated with at least one selected from the group of a bacteria static agent to enable the specimen to be held at room temperature during transit, dyes to enable the subject to determine how much specimen has been deposited relative to volume requirements, dyes to determine if sample degradation has occurred, and inhibitors to prevent the degradation of analytes of primary interest in the specimen.

7. The device of claim 6 further comprising a chamber defined by an outer wall of the elongate tube positioned proximal to the second end of the elongate tube.

8. The device of claim 7 further comprising a filter disposed within the chamber.

9. The device of claim 6 wherein the filter further comprises a polymer blended foam or other material.

10. The device of claim 6 wherein the device further comprises an exhaust port defined by the outer wall of the coupler.

11. The device of claim 6 further comprising a specimen collection vial having a volume capacity of approximately 50 μL to 5 mL.

12. The device of claim 6 wherein the outer wall of the coupler further defines a press fit taper such that the device can be press-fit into collection vials of varying size.

\* \* \* \* \*